(12) United States Patent
Pallaske et al.

(10) Patent No.: US 9,108,336 B2
(45) Date of Patent: Aug. 18, 2015

(54) WOOD TREATING AGENT AND METHOD OF TREATING WOOD OR WOOD BASED MATERIALS OR THE LIKE

(75) Inventors: Michael Pallaske, Steinen (DE); Peter Jüngel, Bad Berleburg (DE); Sascha Hellkamp, Bad Berleburg (DE)

(73) Assignee: Kurt Obermeier GMBH & Co. KG., Bad Berleburg (DE)

( * ) Notice: Subject to any disclaimer, the term of this patent is extended or adjusted under 35 U.S.C. 154(b) by 0 days.

(21) Appl. No.: 13/982,077

(22) PCT Filed: Jan. 24, 2012

(86) PCT No.: PCT/EP2012/000307
§ 371 (c)(1),
(2), (4) Date: Jul. 26, 2013

(87) PCT Pub. No.: WO2012/100937
PCT Pub. Date: Aug. 2, 2012

(65) Prior Publication Data
US 2013/0309517 A1 Nov. 21, 2013

(30) Foreign Application Priority Data
Jan. 28, 2011 (DE) .................. 10 2011 009 678

(51) Int. Cl.
| | |
|---|---|
| *B27K 3/16* | (2006.01) |
| *B27K 3/52* | (2006.01) |
| *A01N 25/32* | (2006.01) |
| *B27K 3/02* | (2006.01) |
| *B27K 5/00* | (2006.01) |

(52) U.S. Cl.
CPC . *B27K 3/52* (2013.01); *A01N 25/32* (2013.01); *B27K 3/0278* (2013.01); *B27K 3/16* (2013.01); *B27K 5/003* (2013.01); *B27K 2240/15* (2013.01); *Y10T 428/662* (2015.04)

(58) Field of Classification Search
CPC .......... B27K 3/52; B27K 3/0278; B27K 3/16; B27K 5/003; B27K 2240/15
USPC ............ 428/532, 537.1; 427/397, 393, 372.2; 106/15.05
IPC ....... B27K 3/16, 3/52, 3/02, 5/00; A01N 25/00, A01N 59/16
See application file for complete search history.

(56) References Cited

U.S. PATENT DOCUMENTS

| | | | | |
|---|---|---|---|---|
| 5,604,339 | A  * | 2/1997 | Tabatabaie-Raissi et al. | 204/157.3 |
| 6,123,756 | A  * | 9/2000 | Poppen et al. | 106/15.05 |
| 6,248,159 | B1 * | 6/2001 | Poppen et al. | 106/15.05 |
| 7,781,638 | B2 * | 8/2010 | Kozliak et al. | 588/313 |
| 8,637,089 | B2 * | 1/2014 | Zhang et al. | 424/630 |
| 2007/0196582 | A1* | 8/2007 | Sinko et al. | 427/397 |

FOREIGN PATENT DOCUMENTS

WO 0023232 A1 4/2000

* cited by examiner

*Primary Examiner* — Leszek Kiliman
(74) *Attorney, Agent, or Firm* — DeLio, Peterson & Curcio, LLC; Robert Curcio (57) ABSTRACT

Wood is treated with at least one photocatalytically degradable organic substance, organic compound or at least one biocide to reduce the contamination by organic substances, organic compounds and/or biocides from wood or wood-base materials into the immediate surroundings, in particular in closed spaces. The wood treatment agent contains at least one photocatalyst which brings about the degradation of the at least one organic substance, organic compound and/or the at least one biocide. The application/introduction of the at least one photocatalyst to or into the wood can take place together with or after the introduction of the wood preservation agent.

12 Claims, 2 Drawing Sheets

WOOD TREATING AGENT AND METHOD OF TREATING WOOD OR WOOD BASED MATERIALS OR THE LIKE

BACKGROUND OF THE INVENTION

1. Field of the Invention

The invention relates to a wood treating agent and to a method of treating wood or wood-based materials or the like. More specifically, the invention relates to wood or a wood-based material or the like and to a use of photocatalysts to degrade organic substances, organic compounds and/or biocides.

2. Description of Related Art

The chemical protection of wood or wood-based materials or the like is accomplished by means of wood preservatives containing biocides. These preservatives are applied to the wood or are introduced into the wood and set up in it very long-lasting biocidal barriers to fungi and insects, which destroy wood. Wood or wood-based materials or the like may also contain organic substances and/or organic compounds.

The introduction of a wood preservative into the wood is performed by, for example, what are referred to as surface treatment processes such for example as brushing, dipping or spraying or by protracted exposure processes such for example as soaking in a tank or by impregnation processes such for example as impregnation in a pressurized vessel. What all these processes have in common is that the wood preservative makes its way into the interior of the wood via the surface thereof and, depending on the process selected, leaves behind it or creates, over a greater or lesser depth, a biocide-charged barrier zone or a barrier zone which is charged with organic substances and/or organic compounds. Within the barrier zone, the distribution of the organic substances and/or organic compounds and/or biocides, which will all also be referred to below as materials, is approximately uniform only in the case of the above-mentioned impregnation processes. In the case of the surface treatment processes and protracted exposure processes there is, as a rule, an exponential decrease in the content of the above-mentioned materials, which is also referred to as the active principle content, inwards from the surface.

In the case of the surface treatment processes, the depth of penetration of the wood preservative is usually approximately 1 to 5 mm and the depth over which it is effective, referred to above as the barrier zone, is usually 0.5 to 3 mm, there being a sharp exponential decrease in the distribution of the above-mentioned materials, and in particular in the biocide distribution, inwards from the surface in the barrier zone.

In the case of the protracted exposure processes, the depth of penetration of the wood preservative is usually approximately 5 to 15 mm, and the depth over which it is effective is 3 to 12 mm, there being a moderate exponential decrease in the distribution of the above-mentioned materials, and in particular in the biocide distribution, inwards from the surface in the barrier zone.

In the case of the impregnation processes, the depth of penetration of the wood preservative is usually more than 20 mm and the depth over which it is effective is likewise more than 20 mm, the distribution of the above-mention materials, and in particular the biocide distribution, being almost uniform in the barrier zone.

Particularly in the above-mentioned surface treatment processes but also in the protracted exposure processes, very high concentrations of the above-mentioned materials occur on and immediately below the treated surface of the wood or wood-based material or the like. The concentration gradient between the surface of the wood and the immediate surroundings causes a transmission of materials from the wood into the surrounding air or onto the suspended matter contained in the air. In enclosed spaces, additional pollution of the air in the spaces by biocides may occur particularly as a result of the desorption of biocide molecules from dust particles. Even if the desorption effects mentioned are only slight, it is desirable for them to be prevented at least in the area directly surrounding dwellings, in order to limit the total biocidal pollution in the immediate environment in which people live or they stay for short periods to a level which is feasible in technical terms. The high biocide concentration on wood surfaces is also a problem wherever treated wood comes into direct contact with humans or animals (patio decking, playgrounds, animal stalls, etc.). Much the same applies to pollution by individual ones or all of the materials mentioned above.

SUMMARY OF THE INVENTION

Bearing in mind the problems and deficiencies of the prior art, it is therefore an object of the present invention to design a wood treating agent of the kind specified in the opening paragraph and a method of the kind specified in the opening paragraph in such a way that the release of organic substances, organic compounds and/or biocides from wood or wood-based materials or the like into the immediate surroundings, and particularly into spaces in which people live, is reduced to a negligible level. The intention is also to provide a wood or wood-based material or the like of the above-mentioned kind whose surface reduces the exposure to organic substances, organic compounds and/or biocides to a level which is feasible in technical terms when in direct contact with humans or animals.

This object is achieved in accordance with the invention by a wood treating agent which has the features, and a method as identified in the claims. Advantageous refinements form the subject matter of the respective sets of dependent claims.

The above and other objects, which will be apparent to those skilled in the art, are achieved in the present invention which is directed to a wood treating agent comprising a wood preservative having at least one organic substance, organic compound, or biocide, or any combination thereof, wherein the at least one organic substance, organic compound, or biocide is photocatalytically degradable, the wood preservative including at least one photocatalyst causing degradation of the at least one organic substance, organic compound, or biocide, or any combination thereof.

The at least one photocatalyst may include titanium dioxide ($TiO_2$), carbon-doped $TiO_2$, nitrogen-doped $TiO_2$, or nitrogen-doped $TiO_2$ having palladium nanoparticles.

The at least one photocatalyst may be suspended in the wood preservative.

The particle size of the at least one photocatalyst is in the range of 10 to $30 \times 10^3$ nm, 100 to $5 \times 10^3$ nm, or 150 to $3 \times 10^3$ nm.

The proportion of the at least one photocatalyst in the wood preservative is in the range of $1 \times 10^{-4}$ to 10% by weight, 0.5 to 5% by weight, or 1 to 3% by weight.

The at least one biocide contains: one or more fungicides selected from the group consisting of: triazoles, imidazoles, thiazole carboxanilides, copper salts, mixed salts, succinate dehydrogenase inhibitors, naphthalene derivatives, sulphonamides, benzimidazoles, thiabendazoles, thiocyanates, quaternary ammonium compounds, morpholine derivatives, iodine derivatives, phenol derivatives, bromine derivatives, isothiazolinones, pyridines or pyrimidines, metal soaps, oxides, dialkyl dithiocarbamates, nitriles, benzothiazoles, quinolines, benzamides, boron compounds, formaldehyde and formaldehyde-releasing compounds, diazenium compounds and/or salts of sorbic acid; or one or more insecticides selected from the group consisting of: phosphoric acid esters, carbamates, organosilicon compounds, pyrethroids, nitroimines and nitromethylenes and/or benzoyl ureas; in a dissolved, emulsified, micro-emulsified, or micro-encapsulated form, or in the form of dispersed particles, or in a form bound in/to micro-particles, or any combination thereof.

In a second aspect, the present invention is directed to a method of treating wood or wood-based materials comprising: applying a wood preservative including at least one organic substance, organic compound, or biocide, or any combination thereof, to the wood or is introduced thereinto; applying to or into the wood at least one photocatalyst causing degradation of the at least one organic substance, organic compound, or biocide, or any combination thereof, the application of the at least one photocatalyst taking place together with or after the application of the wood preservative.

The method including suspending the at least one photocatalyst in the wood preservative, applying the at least one photocatalyst to the wood, or introducing the at least one photocatalyst thereinto together with the wood preservative, or any combination thereof.

The method includes having the particle size of the at least one photocatalyst is in the range of 10 to $30 \times 10^3$ nm, 100 to $5 \times 10^3$ nm, or 150 to $3 \times 10^3$ nm, and is selected in such a way that the at least one photocatalyst applied to the wood penetrates no more than approximately 1 mm into the wood.

In a third aspect, the present invention is directed to a wood or wood-based material having a wood preservative including at least one organic substance, organic compound, or biocide, or any combination thereof, wherein the at least one organic substance, organic compound, or biocide is photocatalytically degradable and the wood includes at least one photocatalyst causing degradation of the at least one organic substance, organic compound, or biocide.

The wood or wood based material includes the at least one photocatalyst having titanium dioxide ($TiO_2$), carbon-doped $TiO_2$, nitrogen-doped $TiO_2$, or nitrogen-doped $TiO_2$ having palladium nanoparticles.

The wood or wood based material including the particle size of the at least one photocatalyst being in the range of 10 to $30 \times 10^3$ nm, 100 to $5 \times 10^3$ nm, or 150 to $3 \times 10^3$ nm, and selected in such a way that the at least one photocatalyst applied to the wood penetrates not more than approximately 1 mm into the wood.

In a fourth aspect, the present invention is directed to a method of degrading organic substances, organic compounds, or biocides, or any combination thereof, in wood having at least one organic substance, organic compound, or biocide, the method using photocatalysts.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DESCRIPTION OF THE PREFERRED EMBODIMENT(S)

In describing the preferred embodiment of the present invention, reference will be made herein to FIGS. 1-4 of the drawings in which like numerals refer to like features of the invention.

The wood treating agent according to the invention contains a wood preservative, which contains at least one organic substance, one organic compound and/or one biocide, the at least one organic substance, organic compound and/or biocide being photocatalytically degradable. The wood treating agent also contains at least one photocatalyst which causes degradation of the at least one organic substance, organic compound and/or biocide. It is possible in this way for residual amounts of one or more of the above-mentioned materials, and in particular residual amounts of biocides, on surfaces of treated wood to be removed by photo-induced or photocatalytic destruction. Because surfaces which have been treated in this way by photo-induced or photocatalytic means no longer have any organic substances, organic compounds and/or biocides, desorption of the relevant particles can thus no longer take place into the surrounding atmosphere and neither can any deposit of the particles concerned onto dust particles. Pollution by one or more of the above-mentioned materials particularly in spaces where people live or they stay for short periods can be very largely reduced and, when humans or animals make direct contact with treated wood, direct exposure to biocides for example is prevented in this way.

In a refinement of the invention, the at least one photocatalyst is or contains titanium dioxide ($TiO_2$), carbon-doped $TiO_2$, nitrogen-doped $TiO_2$, or nitrogen-doped $TiO_2$ having palladium nanoparticles. In a particularly preferred embodiment of the invention, the $TiO_2$ is present in anatase form. The different dopings of the $TiO_2$ mentioned above cause photocatalysis to take place even in the daylight range rather than solely in the ultraviolet (UV) range. The palladium nanoparticles mentioned above act as a sort of "battery" or energy store, and the photocatalysis is thus able to continue to progress even when the lighting conditions are poor and/or even in the dark.

In a particularly preferred embodiment of the invention, the at least one photocatalyst is suspended in the wood preservative, the particle size of the at least one photocatalyst being 10 to $30 \times 10^3$ nm, and preferably 100 to $5 \times 10^3$ nm, and as a particular preference 150 to $3 \times 10^3$ nm, and the proportion of the at least one photocatalyst in the wood preservative is $1 \times 10^{-4}$ to 10% by weight, and preferably 0.5 to 5% by weight, and as a particular preference 1 to 3% by weight. By suspending the photocatalyst in the wood preservative it becomes possible for the wood preservative and photocatalyst to be applied to the surface of the wood in a single stage of operation. The particle size of the at least one photocatalyst can be selected in such a way that the photocatalyst is situated almost exclusively on the surface of the wood or wood-based material or the like and only penetrates into the wood to a small extent. In this way the photocatalyst can be provided precisely where, and largely only where, it can be expected or assumed that the incidence of light will occur.

In another refinement of the invention, the at least one biocide is one or more fungicides selected from: triazoles, imidazoles, thiazole carboxanilides, copper salts, mixed salts, succinate dehydrogenase inhibitors, naphthalene derivatives, sulphonamides, benzimidazoles, thiabendazoles, thiocyanates, quaternary ammonium compounds, morpholine derivatives, iodine derivatives, phenol derivatives, bromine derivatives, isothiazolinones, pyridines or pyrimidines, metal soaps, oxides, dialkyl dithiocarbamates, nitriles, benzothiazoles, quinolines, benzamides, boron compounds, formaldehyde and formaldehyde-releasing compounds, diazenium compounds and/or salts of sorbic acid; and/or is one or more insecticides selected from: phosphoric acid esters, carbamates, organosilicon compounds, pyrethroids, nitroimines and nitromethylenes and/or benzoyl ureas.

This being the case, the above-mentioned photocatalysts are in a position to degrade a large number of fungicides and insecticides and these substances are thus no longer able to make their way from the wood into the immediate surroundings. Much the same applies to the degradation of one or more organic substances and/or compounds.

In the method according to the invention of treating wood or wood-based materials or the like, a wood preservative which contains at least one organic substance organic compound and/or biocide is applied to the wood or is introduced thereinto. The method according to the invention also comprises the further steps of: applying/introducing to or into the wood at least one photocatalyst which causes degradation of the at least one organic substance, organic compound and/or biocide, the application/introduction of the at least one photocatalyst taking place together with or after the application/introduction of the wood preservative.

The first alternative mentioned above in which the at least one photocatalyst is applied to the wood or introduced thereinto together with the wood preservative has the advantage that the at least one photocatalyst can be supplied to the wood not in a separate stage of operation, but simultaneously with the wood preservative. There is thus not usually any need for any independent, i.e. separate, application or introduction of the at least one photocatalyst.

The second alternative mentioned above in which the application/introduction of the at least one photocatalyst takes place after the application/introduction of the wood preservative has the advantage that even wood, which has already been treated with a wood preservative can be provided with the at least one photocatalyst so to speak retrospectively, thus enabling the method according to the invention to be applied even to wood which has already been provided with wood preservative. The method according to the invention can thus be applied even to quite old wood, which has already been treated with a wood preservative.

Advantageously, the at least one photocatalyst is suspended in the wood preservative and is applied to the wood and/or introduced thereinto together with the wood preservative. The wood preservative and the at least one photocatalyst can thus be supplied to the wood in a single stage of operation. This enables the method according to the invention to be carried out particularly inexpensively.

In another refinement of the invention, the particle size of the at least one photocatalyst is 10 to $30 \times 10^3$ nm, and preferably 100 to $5 \times 10^3$ nm, and as a particular preference 150 to $3 \times 10^3$ nm and the particle size is selected in such a way that the at least one photocatalyst applied to the wood penetrates no more than approximately 1 mm into the wood. The at least one photocatalyst is thus situated in a region of the wood close to the surface, namely in the region on which light may also be incident during the lifetime of the wood. The at least one organic substance, organic compound and/or biocide which are positioned further into the interior of the wood can perform their preservative action there unhindered. The action of the at least one photocatalyst at the surface merely prevents them emerging from the wood and interacting with the immediate surroundings of the treated wood.

The wood or wood-based material or the like contains a wood preservative which contains at least one organic substance, organic compound and/or biocide. The at least one organic substance, organic compound and/or biocide is photocatalytically degradable. Also the wood or wood-based material or the like has at least one photocatalyst which causes degradation of the at least one organic substance, organic compound and/or biocide. The wood or wood-based material or the like thus also contains, as well as the at least one organic substance, organic compound and/or the wood preservative containing at least one biocide, at least one photocatalyst. The latter is applied to the wood or introduced thereinto in such a way that the at least one organic substance, organic compound and/or biocide is left in the wood unchanged but is prevented from migrating from the surface of the wood into the surroundings or from coming therefrom into direct contact with humans or animals.

The at least one photocatalyst is that which has already been mentioned above in connection with the wood preservative according to the invention.

The particle size and the selection of the particle size also conform to the particulars which were given above in connection with the wood preservative.

Another aspect of the invention is using photocatalysts to degrade organic substances, organic compounds and/or biocides in wood having at least one organic substance, organic compound and/or biocide.

The wood treating agent contains a wood preservative. The latter contains at least one organic substance, organic compound and/or biocide. The at least one organic substance, organic compound and/or biocide is photocatalytically degradable. The wood treating agent also contains at least one photocatalyst 1 which, under suitable conditions, namely when light is incident upon it, causes degradation of the at least one organic substance, organic compound and/or biocide.

The at least one photocatalyst 1 is or contains titanium dioxide ($TiO_2$), carbon-doped $TiO_2$, nitrogen-doped $TiO_2$, or nitrogen-doped $TiO_2$ having palladium nanoparticles.

Other inorganic photocatalysts are or contain ZnO, $WO^3$, $SnO_2$, $Fe_2O_3$, FeOOH, $Al_2O_3$, Si, $SiO_2$, $ZrO_2$, $M_oO_3$, CdS.

Other organic photocatalysts are or contain indanthrone, phthalocyanines and metal complexes thereof, quinacridone and/or perylene tetracarboxylic dianhydride, alone or in combination with $TiO_2$.

Other organic photoinitiators are or contain benzyl dimethyl ketal, the class of cyclohexyl phenyl ketones and/or the class of acyl phosphine oxides.

Under UV light or under daylight, the at least one photocatalyst is capable of collecting light energy and then also introducing it into biocide molecules and, where they are present, into residual amounts of organic substances and/or organic compounds, such as into residual amounts of solvents, and thus of destroying them. Residual amounts of solvents may be of, for example, glycols, amino alcohols and/or glycol ethers.

In a particularly preferred embodiment, the at least one photocatalyst is suspended in the wood preservative. Preferably, the particle size of the at least one photocatalyst in the suspension is 10 to $30\times10^3$ nm, and preferably 100 to $5\times10^3$ nm, and as a particular preference 150 to $3\times10^3$ nm. Particle size is also referred to as pigment size. The proportion of the at least one photocatalyst in the wood preservative is $1\times10^4$ to 10% by weight, and preferably 0.5 to 5% by weight, and as a particular preference 1 to 3% by weight. This being the case, the proportion of the at least one photocatalyst in the wood preservative gives the pigment content of the photocatalyst in the wood preservative.

The at least one biocide contains one or more fungicides and/or one or more insecticides.

The one or more fungicides comprise for example: triazoles such as amitrole, azocyclotin, BAS 480F, bitertanol, difenoconazole, fenbuconazole, fenchlorazole, fenethanil, fluquinconazole, flusilazole, flutriafol, imibenconazole, isazofos, myclobutanil, opus, paclobutazol, penconazole, tetraconazole, tridiamefon, tridiamenol, triapenthenol, triflumizole, uniconazole; 2-(1-chloro-cyclopropyl)-1-(2-chlorophenyl)-3-(1H-1,2,4-triazol-1-yl)propan-2-ol, 2-(tert-butyl)-1-(2-chloro-phenyl)-3-(1H-1,2,4-triazol-1-yl)propan-2-ol, (±)-cis-1-(4-chlorophenyl)-2-(1H-1,2,4-traizol-1-yl) cycloheptanol, azaconole: 1-([2-(2,4-dichlorophenyl)-1,3-dioxolan-2-yl]methyl)-1H-1,2,4-triazole, propiconazole: 1-[2-(2,4-dichlorophenyl)-4-propyl-1,3-dioxolan-2-yl]methyl-1H-1,2,4-triazole, tebuconazole: 1-p-chlorophenyl-4,4-dimethyl-3 (1H-1,2,4-triazol-1-yl-methyl)pentan-3-ole, cyproconazole: 2-(4-chlorophenyl)-3-cyclopropyl-1-(1H-1,2,4-triazol-1-yl)butan-2-ole, metconazole: 5-[(4-chlorophenyl)methyl]-2,2-dimethyl-1-(1H-1,2,4-triazol-1-ylmethyl) cyoclopentanol;

imidazoles, such as: imazalil, pefurazoate, prochloraz, triflumizole, 2-(1-tert-butyl)-1-(2-chlorophenyl)-3-(1,2,4-triazol-1-yl)propan-2-ol; thiazole carboxanilides, such as 2',6'-dibromo-2-methyl-4-trifluoromethoxy-4'-trifluoromethyl-1,3-thiazole-5-carboxanilide;

copper salts, such as: copper sulphate, copper carbonate, copper hydroxide carbonate, copper dihydroxide, copper chloride, copper-ammonium complexes, copper amine complexes, copper-diazenium complexes, and copper sulphate, copper carbonate, copper hydroxide carbonate, and copper chloride as particles in a micronized form (particle size from 30 nm to 50 μm, and preferably from 100 nm to 500 nm);

mixed salts, such as: copper/boron mixtures, copper/chromium/boron mixtures, copper/chromium/arsenic mixtures;

succinate dehydrogenase inhibitors, such as: fenfuram, furcarbanil, cyclafluramid, funnecyclox, seedvax, metsulfovax, pyrocarbolide, oxycarboxin, Shirlan, mebenil (mepronil), benodanil, flutolanil (Moncut);

naphthalene derivatives such as: terbinafines, naftifines, butenafines, 3-chloro-7-(2-aza-2,7,7-trimethyl-oct-3-en-5-in;

sulphenamides, such as: dichlorofluanid, tolylfluanid, folpet, fluorofolpet, captan, captofol;

benzimidazoles such as: carbendazim, benomyl, furathiocarb, fuberidiazole, thiophonate methyl; thiabendazoles or salts thereof;

thiocyanates such as: thiocyanatomethyl thiobenzothiazole, methylene bisthiocyanate;

quaternary ammonium compounds such as: alkyl dimethyl benzyl ammonium chloride, propionate and/or carbonate, benzyl dimethyl tetradecyl ammonium chloride, propionate and/or carbonate, benzyl dimethyl dodecyl ammonium chloride, propionate and/or carbonate, didecyl dimethyl ammonium chloride, propionate and/or carbonate, coco alkyl trimethyl ammonium chloride, propionate and/or carbonate, didecylmethylpoly(oxyethyl)ammonium chloride, propionate and/or carbonate, morpholine derivatives such as: tridemorph, fenpropimorph, falimorph, dimethomorph, dodemorph, aldimorph, fenpropidin, and salts thereof formed with aryl sulphonic acids such for example as toluene sulphonic acid and p-dodecyl phenyl sulphonic acid;

iodine derivatives such as: diiodomethyl-p-sulfone, 3-iodo-2-propinyl alcohol, 4-chlorophenyl-3-iodopropargyl-formal, 3-bromo-2,3-diiodo-2-propenylethyl carbamate, 2,3,3-triiodoallyl alcohol, 3-bromo-2,3-diiodo-2-propenyl alcohol, 6-iodo-3-oxohex-5-in-olbutyl carbamate, 6-iodo-3-oxohex-5-in-oJ-phenyl carbamate, 3-iodo-2-propinyl-n-hexyl carbamate, 3-iodo-2-propinylcyclohexyl carbamate, 3-iodo-2-propinylphenyl carbamate, 3-iodo-2-propinylbutyl carbamate;

phenol derivatives such as: tribromophenol, tetrachlorophenol, 3-methyl-4-chlorophenyl, dichlorophen, o-phenyl phenol, m-phenyl phenol, p-phenyl phenol, 2-benzyl-4-chlorophenol;

bromine derivatives such as: 2-bromo-2-nitro-1,3-propane diol;

isothiazolinones such as: N-methyl isothiazolin-3-one, 5-chloro-N-methyl isothiazolin-3-one, 4,5-dichloro-N-octyl isothiazolin-3-one, 4,5-dichloro-2-octyl-2H-isothiazol-3-one, N-octyl isothiazolin-3-one, benzoisothiazolinone, 4,5-trimethylene isothiazolinone;

pyridines or pyrimidines such as: 1-hydroxy-2-pyridinethione (and salts thereof formed with Na, Fe, Mn, Zn), tetrachloro-4(methyl-sulfonyl)pyridine, pyrimethanil, mepanipyrim, dipyrithione;

metal soaps such as: tin, copper or zinc naphthenate, octoate, 2-ethyl hexanoate, oleate, phosphate or benzoate;

oxides such as: tributyl tin oxide, $Cu_2O$, CuO, ZnO;

dialkyl diothiocarbamates such as: Na and Zn salts of dialkyl diothiocarbamates, tetramethyl thiuram disulphide, dithio carbamates, cufraneb, ferbam, mancopper, mancozeb, maneb, metam, metiram, thiram, zineb, ziram;

nitriles such as: 2,4,5,6-tetrachloroisophthalodinitrile, 2,3,5,6-tetra-fluoroterephthalodinitrile;

benzothiazoles such as: 2-mercaptobenzothiazole;

quinolines such as: 8-hydroxyquinoline and salts thereof formed with copper;

benzamides such as: 2-6-dichloro-N-(4-trifluoromethylbenzyl)benzamide (XRD-563);

boron compounds such as: boric acid, boric acid esters, borax, boron oxide, disodium octoborate tetrahydrate, disodium tetraborate;

formaldehyde and formaldehyde releasing compounds such as: benzyl alcohol mono(poly)hemiformal, oxazolidine, hexahydro-s-triazine, N-methylol chloroacetamide, paraformaldehyde, nitropyrin, oxalinic acid, tecloftalam;

diazenium compounds such as: tris-N-(cyclohexyldiazeniumdioxy)aluminium, N(cyclohexyl-diazeniumdioxy)tributyl tin or salts thereof formed with K, bis-N-(cyclohexyldiazeniumdioxy)copper;

and/or salts of sorbic acid such as: sodium sorbate, potassium sorbate.

Other fungicides may be selected from one or more of the following materials: acypetacs, 2-aminobutane, ampropylfos, anilazine, benalaxyl, bupirimate, quinomethionate, chlorfenapyr, chloroneb, chlozolinate, cymoxanil, dazomet, diclomezine, dichlofluanid, dichioram, diethofencarb, dimethirimol, dinocarb, dithianon, dodine, drazoxolon, edifenphos, ethirimol, etridiazole, fenarimol, fenitropan, fentin acetate, fentin hydroxide, ferimzone, fluazinam, fluoromide, flusulfamide, flutriafol, fosetyl, fthalide, furalaxyl, glutaraldehyde, guazatine, hymexazol, iprobenfos, iprodione, isoprothiolane, metalaxyl, methasulfocarb, nitrothal-isopropyl, nuarimol, ofurace, oxadiyl, pefflurazoate, pencycuron, phosdiphen, pimaricin, piperalin, procymidone, propamocarb, propineb, pyrazophos, pyrinfenox, pyroquilon, quintozene, tar oils, tecnazene, thicyofen, thiophanate methyl, tolclofos methyl, tolyl fluanide, triazoxide, trichlamide, tricyclazole, triforine, vinclozolin.

The one or more insecticides comprise for example: phosphoric acid esters such as: azinphos ethyl, azinphos methyl, a-1(4-chlorophenyl)-4-(O-ethyl, S-propyl)phosphoryloxy-pyrazole, chlorpyrifos, coumaphos, demeton, demeton-5-methyl, diazinone, dichlorvos, dimethoate, ethoate, ethoprophos, etrimfos, fenitrothion, fenthion, heptenophos, parathion, parathion methyl, phosalone, phoxim, pirimiphos ethyl, pirimiphos methyl, profenofos, prothiofos, sulfprofos, triazophos or trichlorophon;

carbamates such as: aldicarb, bendiocarb, a-2-(1-methylpropyl)phenyl methyl carbamate, butocarboxim, butoxycarboxim, carbaryl, carbofuran, carbosulfan, cloethocarb; isoprocarb, methomyl, oxamyl, pirimicarb, promecarb, propoxur or thiodicarb;

organosilicon compounds, preferably ones such as: dimethyl(phenyl)silylmethyl-3-phenoxybenzyl ethers such as dimethyl(4-ethoxyphenyl)silylmethyl-3-phenoxybenzyl ether or (dimethylphenyl)silylmethyl-3-phenoxy-6-pyridylmethyl ethers such for example as dimethyl-(9-ethoxyphenyl)silylmethyl-2-phenoxy-6-pyridylmethyl ether or [(phenyl)-3-(3-phenoxyphenyl)propyl](dimethyl)silanes such for example as (4-ethoxyphenyl)-[3-(4-fluoro-3-phenoxyphenylpropyl]dimethyl silane, silafluofen;

pyrethroids such as: allethrin, alphamethrin, bioresmethrin, byfenthrin, cycloprothrin, cyfluthrin, descamethrin, cyhalothrin, cypermethrin, deltamethrin, alpha-cyano-3-phenyl-2-methylbenzyl-2,2-dimethyl-3-(2-chloro-2-trifluoromethyl vinyl)cyclopropane carboxylate, etofenprox, fenpropathrin, fenfluthrin, fenvalerate, flucythrinate, flumethrin, fluvalinate, permethrin, pyrethrum, resmethrin and tralomethrin;

nitroimines and nitromethylenes such as: 1-[(6-chloro-3-pyridinyl)methyl]-4,5-dihydro-N-nitro-1H-imidazol-2-amine (imidacloprid), N-[(6-chloro-3-pyridyl)methyl]N$^2$-cyano-N$^1$-methyl acetamides (N=1-25); and/or benzoyl ureas such as: chlorfluazuron, diflubenzuron, flufenoxuron, flucycloxuron, hexaflumoron, penfluoron, teflubenzuron, triflumuron and other inhibitors of development such for example as benzoic acid, [2-benzoyl-1-(1,1-dimethylethyl)hydrazide, 2,6-dimethoxy-N-[5-]4-(pentafluoroethoxy)phenyl-[2,3,4-thiadiazol-2-yl]benzamide, N-cyclopropyl-1,3,5-triazin-2,4-triamine, 2-(4-phenoxyphenoxy)ethylethyl carbamate, 1-(decycloxy)-4-[(6-methoxy-4-hexinyl)oxy]benzene, (2-propinyl)-4-methoxy benzoate, fenoxycarb, pyriproxyfen, triarathene, thiapronil, hexythiazox, clofentezine, 4-chloro-5-(6-chloro-3-pyridylmethoxy)-2-(3,4-dichlorophenyl)pyridazin-3(2H)one, buprofezin, hydroprene, kinoprene, methoprene, cyclorpate, gusathin, padan, paraxon, tribunil and triprene.

Other insecticides can be selected from one or more of the following substances: abamectin, AC 303,630, acephate, acrinathrin, alanycarb, aldoxycarb, aldrin, ammonium bifluoride, amitraz, azamethiphos, Bacillus thuringiensis, phosmet, phosphamidon, phosphine, prallethrin, propaphos, propetamphos, prothoate, pyraclofos, pyrethrins, pyridaben, pridafenthion, pyriproxyfen, quinalphos, RH-7988, rotenone, sulfotep, tar oil, teflubenzuron, tefluthrin, temephos, terbufos, tetrachlorvinfos, tetramethrin, o-2-tert-butyl pyrimidin-5-yl-o-isopropyl phosphorothiate, thiacloprid, thiocyclam, thiofanox, thiometon, tralomethrin, triflumuron, trimethacarb, vamidothion, xylylcarb, benfuracarb, bensultap, bifenthrin, bioallethrin, MERbioallethrin (S)-cyclopentyl isomer, bromophos, bromophos ethyl, buprofezin, cadusafos, calcium polysulphide, carbophenothion, cartap, quinomethionate, chlordane, chlorfenvinphos, chlorfluazuron, chlormephos, chloropicrin, chlorpyrifos, cyanophos, beta-cyfluthrin, alphacypermethrin, cyophenothrin, cyromazine, dazomet, DDT, demeton-5-methyl sulfone, diafenthiuron, dialifos, dicrotophos, diflubenzuron, dinoseb, dioxabenzofos, diaxacarb, DNOC, empenthrin, endosulfan, EPN, esfen valerate, ethiofencarb, ethion, etofenprox, fenobucarb, fenoxycarb, fensulfothion, fipronil, flucycloxuron, flufenprox, flufenoxuron, fonofos, formetanate, formothion, fosmethilan, furathiocarb, heptachlor, hexaflumuron, hydramethylnon, hydroprene, IPSP, isazofos, isofenphos, isoprothiolane, isoxathion, iodfenphos, kadethrin, lindane, malathion, mecarbam, mephosfolan, metam, methacrifos, methamidophos, methidathion, methiocarb, methoprene, methoxychlor, methyl isothiocyanate, metholcarb, mevinphos, monocrotophos, naled, nicotine, omethoate, oxydemeton-methyl, pentochlorophenol, phenothrin, phenthoate, phorate.

This being the case, the at least one biocide may act as a fungicide or as an insecticide or may act as a fungicide and an insecticide. Suitable mixtures of the materials cited above as fungicides and insecticides may also be used.

A method of treating wood or wood-based materials or the like will be explained in detail below.

In this method, a wood preservative which contains at least one organic substance, one organic compound and/or one biocide is applied to the wood 2 and/or is introduced thereinto. The term "wood" is used below as an abbreviated form of the terms "wood, wood-based materials or the like."

The method includes the further steps of: application/introduction to/into the wood of the at least one photocatalyst which causes degradation of the at least one organic substance, organic compound and/or biocide, the application/introduction of the at least one photocatalyst taking place together with the application/introduction of the wood preservative or thereafter.

This being the case, the at least one photocatalyst can be brought into contact with the wood simultaneously with, or "together with" as it is phrased above, the wood preservative. For this purpose, the at least one photocatalyst is suspended in the wood preservative in a preferred embodiment of the invention and is applied to the wood and/or introduced thereinto together with the wood preservative. This being the case, the application/introduction of the wood preservative containing at least one photocatalyst can be performed by means of a single stage of operation.

As an alternative to this, it is also possible for the at least one photocatalyst to be applied to the wood or introduced thereinto after the wood preservative in time. This being the case, wood which has already been treated with wood preservative can be post-treated by the application/introduction of the at least one photocatalyst in order to reduce the pollution of the surrounding atmosphere by an organic substance, an organic compound and/or a biocide from the wood, namely particularly in spaces such as rooms in residences.

The particle size of the at least one photocatalyst is 10 to $30 \times 10^3$ nm, and preferably 100 to $5 \times 10^3$ nm, and as a particular preference 150 to $3 \times 10^3$ nm and it is selected in such a way that the at least one photocatalyst applied to the wood penetrates no more than approximately 1 mm into the wood. This will be explained more exactly below.

The wood 2 thus contains a wood preservative which contains at least one organic substance, one organic compound and/or one biocide. The above-mentioned materials are preferably non-photostable. The wood 2 also has a photocatalyst 1 which causes degradation of the at least one organic substance, organic compound and/or biocide. The at least one photocatalyst 1 is or contains titanium dioxide ($TiO_2$), carbon-doped $TiO_2$, nitrogen-doped $TiO_2$, or nitrogen-doped $TiO_2$ having palladium nanoparticles and in particular palladium in the form of metallic nanoparticles.

The particle size of the at least one photocatalyst 1 is 10 to $30 \times 10^3$ nm, and preferably 100 to $5 \times 10^3$ nm, and as a particular preference 150 to $3 \times 10^3$ nm in the wood. The particle size, also referred to as the pigment size, is selected in such a way that the at least one photocatalyst applied to the wood penetrates no more than approximately 1 mm into the wood 2 from the surface 3 thereof.

The invention also covers the use of photocatalysts to degrade organic substances, organic compounds and/or biocides in wood having at least one organic substance, organic compound and/or biocide.

When the at least one photocatalyst is applied or introduced, alone or together with the wood preservative, the liquid front penetrates into the wood together with the at least one organic substance, organic compound and/or biocide. Where application takes place together with the wood preservative, the particles of the at least one photocatalyst are suspended in the wood preservative, and are screened out at the surface of the wood, i.e. the particles of the at least one photocatalyst, depending on the particle size which was selected and set, are left mainly on the surface of the wood and penetrate only approximately 0.5 to 1 mm into the wood. The at least one photocatalyst thus collects in a region close to the surface and is at a high concentration there. The depth of penetration of the at least one photocatalyst is approximately the same as the depth to which light penetrates into the wood, namely preferably 0.5 to 1 mm. Eighty percent (80%) of the at least one organic substance, organic compound and/or biocide is usually situated within a depth of penetration of 2 to 3 mm on or rather in the wood. This being the case, the region close to the surface in particular is heavily charged with the at least one organic substance, at least one organic compound and/or at least one biocide.

Figure 1:
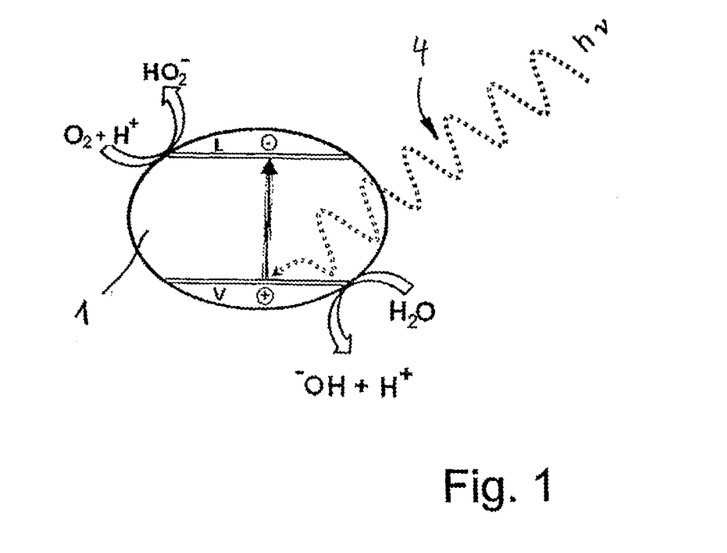
FIG. 1 is a schematic representation of photocatalysis on a photocatalyst.

FIG. 1 is a diagram showing how photocatalysis works at a photocatalyst pigment, namely a $TiO_2$ pigment. The electronic band structure of a semiconductor is characterized by the highest filled energy band, known as the valence band V, and the lowest unfilled energy band, known as the conduction band L. These energy bands are separated by an energy gap.

If, as a result of the incidence of light 4, the semiconductor then absorbs photons whose energy is equal to or greater than the energy gap, electrons in the valence band V are excited to migrate into the conduction band. An excess of electrons forms in the conduction band L and holes left by electrons therefore form in the valence band V. These electron/hole pairs are able to recombine or react at the surface with electron acceptors and electron donors respectively, as is indicated in FIG. 1 by adsorbed water and oxygen. The radicals which are produced are highly reactive materials. They soon attack surrounding substances, such as the materials mentioned above, and in particular biocides. They are also able to operate as what are referred to as bactericides and also as microbicides by attacking and killing bacteria, or are able to cause a self-cleaning function to be performed on the surface of the wood by destroying other organic substances (e.g. auxiliary solvents, materials contained in the wood, dust) and/or organic compounds which escape from the wood or deposit thereon. This being the case, the at least one photocatalyst applied to the wood is also able to perform a disinfecting or sterilizing or conserving action and/or to cause self-cleaning to occur close to the surface.

The semiconductor remains unchanged when the reaction occurs. As well as the degradation of pollutants by radicals, what is also possible is direct oxidation or reduction of organic substances, organic compounds and/or biocides which are adsorbed at the surface of the semiconductor or which are immediately adjacent thereto. The photocatalytic degradation of organic substances, organic compounds and/or biocides can take place both reductively, by means of direct reduction by the electrons in the conduction band L for example, and also oxidatively, by means of the oxidation of the pollutant by OH radicals for example.

In the end, the at least one organic substance, and/or the at least one organic compound and/or the at least one biocide are/is destroyed by radicals as a result of these processes.

In a preferred embodiment of the invention, the particle size of the at least one photocatalyst is selected in such a way that the photocatalyst is set to the desired distribution in the wood.

Figure 2:
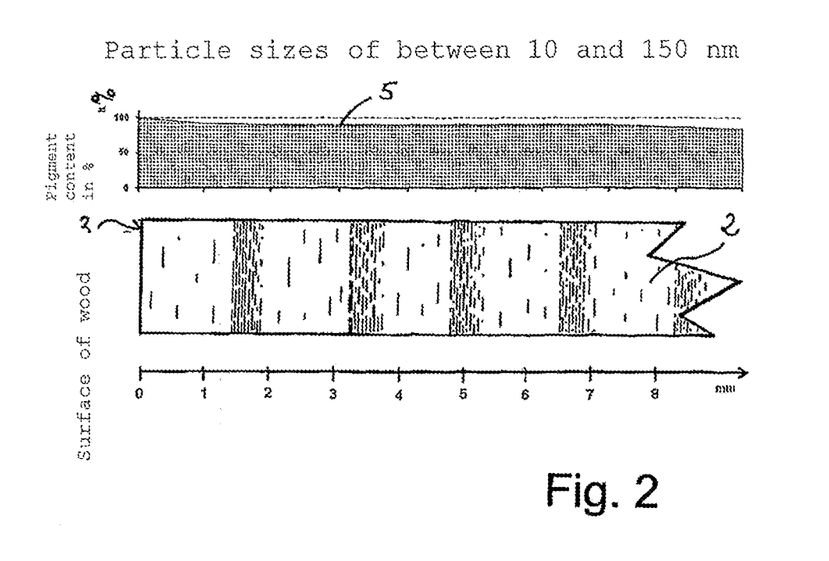
FIG. 2 is a schematic graph in which pigment content is plotted against the depth of penetration of the photocatalyst into wood, this graph relating to a particle size for the photocatalyst of between 20 and 150 nm.
Figure 3:
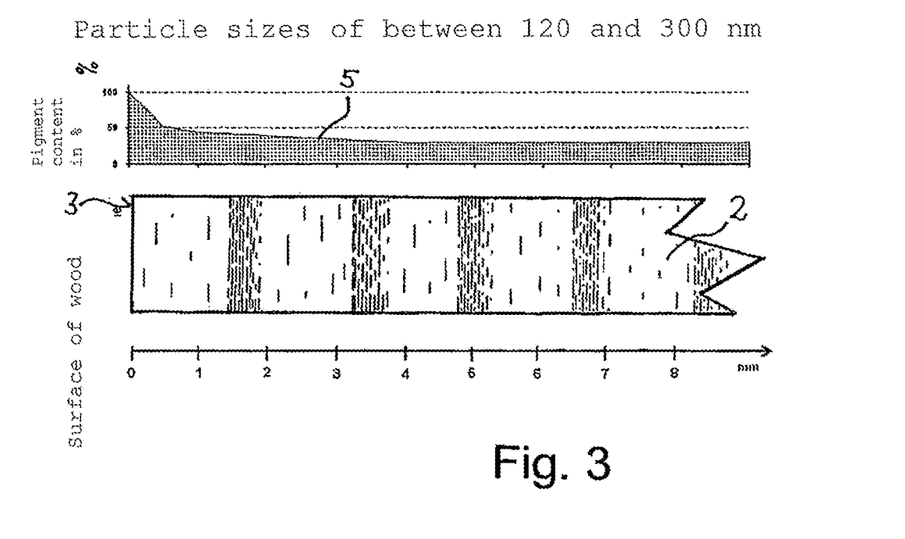
FIG. 3 is a schematic graph in which pigment content is plotted against the depth of penetration of the photocatalyst into wood, this graph relating to a particle size for the photocatalyst of between 120 and 300 nm.
Figure 4:
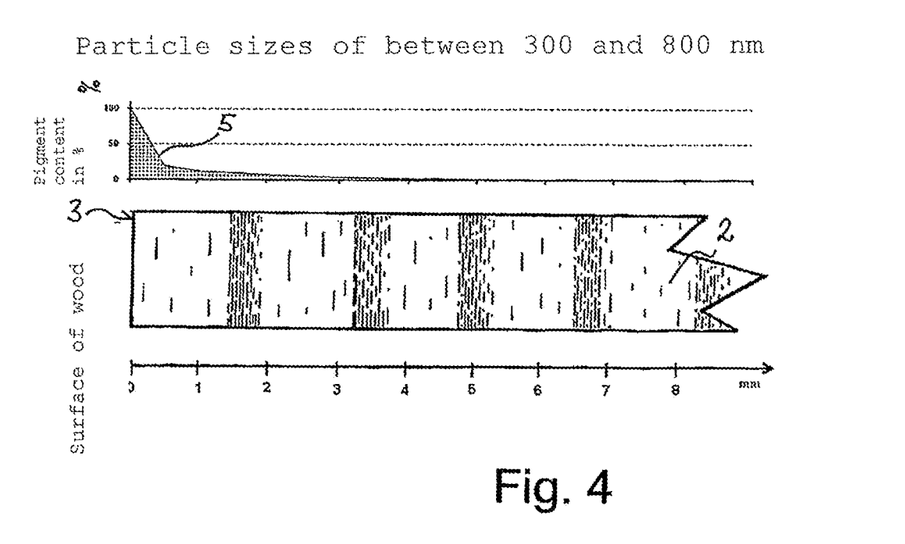
FIG. 4 is a schematic graph in which pigment content is plotted against the depth of penetration of the photocatalyst into wood, this graph relating to a particle size for the photocatalyst of between 300 and 800 nm.

In each of FIGS. 2 to 4, the pigment distribution of the photocatalyst in the wood 2 is shown diagrammatically. Pigment content is plotted in each case against depth of penetration, with the surface 3 of the wood 2 being situated on the left in each of the representations. The depth of penetration of the photocatalyst thus increases from left to right.

In FIG. 2, the particle size of the photocatalyst is 20 to 150 nm. The result is the curve 5 for pigment distribution which is shown in the top part of FIG. 2. This curve shows that the photocatalyst particles are present in the wood relatively evenly over its cross-section. Directly at the surface the particle content, also referred to as the pigment content, is approximately 100%. At a depth of penetration of between 1 and approximately 7 mm, it then drops to approximately 90% and at a depth of penetration of more than 7 mm there is then another slight drop to approximately 80%. It follows from this that photocatalysts of particle sizes of between 20 and 150 nm very largely penetrate into the wood.

The plot in FIG. 3 relates to photocatalysts of particle sizes of between 120 and 300 nm. In this case, the curve 5 to which the pigment distribution sets itself is shown likewise in the top part of the drawing. It can be seen that by a depth of penetration of approximately 0.5 mm the pigment content has dropped from 100 to approximately 50% and between depths of penetration of 0.5 mm and approximately 4 mm it is reduced to a pigment content of approximately 25%. Below a depth of penetration of approximately 4 mm, the pigment content remains constant at approximately 25%.

FIG. 4 shows the curve 5 for pigment distribution for photocatalyst particle sizes of between 300 and 800 nm. Down to a depth of penetration of approximately 0.5 mm there is a steep decline in the pigment content from 100 to approximately 20%. At a depth of penetration of more than 0.5 mm, the curve 5 approaches a pigment content of approximately 0% asymptotically, this content being reached at a depth of penetration of between 4 and 5 mm. FIG. 4 thus first shows a relatively steep decline in the pigment content of the at least one photocatalyst down to a depth of penetration of 0.5 mm.

Thus, by mixing photocatalytic pigments of different size fractions it is possible to control the penetration properties of the photocatalyst in a targeted way, thus enabling the photocatalytic effects to be maintained by the combined use of smaller, deeply penetrating photocatalyst pigments after for example work (sanding, planning, etc.) has been done on the surface of the wood.

The photocatalyst may exist in particulate foam and/or in particulate form fixed to an inert carrier material and/or may be embedded in an inert carrier material. The carrier material may for example be an inert binder or a stratified silicate.

The retrospective application of the photocatalyst may be performed in the same way as was described above in the case of the wood preservative, i.e. by surface treatment processes such as brushing, dipping or spraying or by protracted exposure processes such as soaking in a tank or by impregnation processes such as impregnation in a pressurized vessel.

The at least one biocide may exist in a dissolved, emulsified, micro-emulsified or micro-encapsulated form or in a form where it is dispersed particles or is bound in/to microparticles.

The patterns of distribution shown in FIGS. 2 to 4 apply to pine sapwood which has been treated by a process in a pressurized vessel. The particle size of the at least one photocatalyst can thus be selected in such a way that it is not possible for the photocatalyst particles to penetrate through what are called pit apertures in the wood and the individual particles of the at least one photocatalyst thus collect on the surface 3 of the wood.

The wood is still permeable to water vapor after the application of the wood preservative; it therefore remains open to diffusion.

If the at least one photocatalyst is applied to the surface of the wood then, as soon as the photocatalytic effect described above has occurred, there are hardly any residual amounts of the at least one organic substance, organic compound and/or biocide still situated on the surface. It follows from this that the residual amounts of the above-mentioned materials are no longer able to make their way from surface of the wood into or onto the immediate surroundings and in this way pollution by at least one organic substance, organic compound and/or biocide is very largely reduced in spaces where people live or stay for brief periods and, where there is direct contact with humans or animals, direct exposure to at least one organic substance, organic compound and/or biocide is almost entirely prevented.

As mentioned, the application/introduction of the photocatalyst can take place together with the wood preservative in a single stage or can also take place after the application/introduction of the wood preservative, in two stages.

What is meant by the term "wood preservative" is agents which prevent wood and wood-based materials from losing their value or being destroyed and thus ensure a long useful life for the wood.

It should also be pointed out that the wavelength of the light directed on for decontamination is matched to the absorption characteristics of the biocides used and the photocatalysts used and that daylight and/or artificial light conforms to the absorption characteristics of the photocatalysts used.

Preferably but not exclusively, the organic substances and/or organic compounds and/or biocides used are ones which are non-photostable, i.e. which are unstable when acted on by light.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A wood treating agent comprising a wood preservative having at least one organic substance, organic compound, or biocide, or any combination thereof, wherein the at least one organic substance, organic compound, or biocide is photocatalytically degradable, said wood preservative including at least one photocatalyst causing degradation of the at least one organic substance, organic compound, or biocide, or any combination thereof, said at least one photocatalyst including titanium dioxide ($TiO_2$), carbon-doped $TiO_2$, nitrogen-doped $TiO_2$, or nitrogen-doped $TiO_2$ having palladium nanoparticles.

2. The wood treating agent of claim 1, including the at least one photocatalyst being suspended in the wood preservative.

3. The wood treating agent of claim 1 wherein the particle size of the at least one photocatalyst is in the range of 10 to $30 \times 10^3$ nm, 100 to $5 \times 10^3$ nm, or 150 to $3 \times 10^3$ nm.

4. The wood treating agent of claim 2, wherein the proportion of the at least one photocatalyst in the wood preservative is in the range of $1 \times 10^{-4}$ to 10% by weight, 0.5 to 5% by weight, or 1 to 3% by weight.

5. The wood treating agent of claim 1 wherein the at least one biocide contains:
   one or more fungicides selected from the group consisting of: triazoles, imidazoles, thiazole carboxanilides, copper salts, mixed salts, succinate dehydrogenase inhibitors, naphthalene derivatives, sulphonamides, benzimidazoles, thiabendazoles, thiocyanates, quaternary ammonium compounds, morpholine derivatives, iodine derivatives, phenol derivatives, bromine derivatives, isothiazolinones, pyridines or pyrimidines, metal soaps, oxides, dialkyl dithiocarbamates, nitriles, benzothiazoles, quinolines, benzamides, boron compounds, formaldehyde and formaldehyde-releasing compounds, diazenium compounds and/or salts of sorbic acid;
   or one or more insecticides selected from the group consisting of: phosphoric acid esters, carbamates, organosilicon compounds, pyrethroids, nitroimines and nitromethylenes and/or benzoyl ureas;
   in a dissolved, emulsified, micro-emulsified, or micro-encapsulated form, or in the form of dispersed particles, or in a form bound in/to micro-particles, or any combination thereof.

6. A method of treating wood or wood-based materials comprising:
   applying a wood preservative including at least one biocide to the wood or introduced thereinto;
   applying to or into the wood at least one photocatalyst which can cause degradation of the at least one biocide, the application of the at least one photocatalyst taking place together with or after the application of the wood preservative, said at least one photocatalyst including titanium dioxide ($TiO_2$), carbon-doped $TiO_2$, nitrogen-doped $TiO_2$, or or nitrogen-doped $TiO_2$ having palladium nanoparticles.

7. The method of claim 6, including suspending the at least one photocatalyst in the wood preservative, applying the at least one photocatalyst to the wood, or introducing said at least one photocatalyst thereinto together with the wood preservative, or any combination thereof.

8. The method of claim 6 wherein the particle size of the at least one photocatalyst is in the range of 10 to $30 \times 10^3$ nm, 100 to $5 \times 10^3$ nm, or 150 to $3 \times 10^3$ nm, and is selected in such a way that the at least one photocatalyst applied to the wood penetrates no more than approximately 1 mm into the wood.

9. Wood or wood-based material having a wood preservative including at least one biocide, wherein the at least one biocide is photocatalytically degradable and the wood includes at least one photocatalyst which can cause degradation of the at least one organic substance, organic compound, or biocide, said at least one photocatalyst including titanium dioxide ($TiO_2$), carbon-doped $TiO_2$, nitrogen-doped $TiO_2$, or nitrogen-doped $TiO_2$ having palladium nanoparticles.

10. The wood or wood based material of claim 9, including the particle size of the at least one photocatalyst being in the range of 10 to $30 \times 10^3$ nm, 100 to $5 \times 10^3$ nm, or 150 to $3 \times 10^3$ nm, and selected in such a way that the at least one photocatalyst applied to the wood penetrates not more than approximately 1 mm into the wood.

11. A method of degrading biocides in wood having at least one biocide, said method using photocatalysts, said photocatalysts including titanium dioxide ($TiO_2$), carbon-doped $TiO_2$, nitrogen-doped $TiO_2$, or nitrogen-doped $TiO_2$ having palladium nanoparticles.

12. The method of claim 7 wherein the particle size of the at least one photocatalyst is in the range of 10 to $30 \times 10^3$ nm, 100 to $5 \times 10^3$ nm, or 150 to $3 \times 10^3$ nm, and is selected in such a way that the at least one photocatalyst applied to the wood penetrates no more than approximately 1 mm into the wood.

* * * * *